United States Patent [19]
Yoshikami

[11] Patent Number: 5,376,551
[45] Date of Patent: Dec. 27, 1994

[54] APPARATUS FOR USING FLUORESCENTLY LABELED LIGANDS IN STUDYING INTERACTION OF A NATIVE LIGAND AND ITS RECEPTOR

[75] Inventor: Doju Yoshikami, Salt Lake City, Utah

[73] Assignee: University of Utah Research Foundation, Salt Lake City, Utah

[21] Appl. No.: 80,342

[22] Filed: Jun. 21, 1993

Related U.S. Application Data

[63] Continuation-in-part of Ser. No. 668,237, Mar. 12, 1991, Pat. No. 5,252,492.

[51] Int. Cl.$^5$ .................. G01N 21/64; G01N 21/00; C12Q 1/00
[52] U.S. Cl. ........................... 436/56; 422/58; 422/59; 422/82.07; 422/82.08; 436/514; 436/515; 436/529; 436/530; 436/535
[58] Field of Search .................. 422/55, 56, 58, 82.07, 422/82.08, 59; 436/514, 515, 529, 530, 535

[56] References Cited

U.S. PATENT DOCUMENTS

| | | | |
|---|---|---|---|
| 4,138,474 | 2/1979 | Updike | 436/535 |
| 4,257,884 | 3/1981 | Lim | 436/535 |
| 4,348,894 | 8/1983 | Yamamoto | 436/514 |
| 4,752,562 | 6/1988 | Sherman et al. | 436/515 |
| 4,844,869 | 7/1989 | Glass | 436/535 |
| 4,874,691 | 10/1989 | Chandler | 436/535 |
| 5,063,178 | 11/1991 | Toomey | 422/82.07 |
| 5,143,066 | 9/1992 | Komives et al. | 422/55 |
| 5,183,740 | 2/1993 | Ligler et al. | 436/524 |
| 5,252,494 | 10/1993 | Walt | 436/535 |

OTHER PUBLICATIONS

Pharmacia Catalogue, 1988. pp. 86, 87 & 108. 1988.
Furr et al, Anal. Biochem. 171, 360–365. 1988.

Primary Examiner—Christine M. Nucker
Assistant Examiner—Chris Dubrule
Attorney, Agent, or Firm—Terry M. Crellin

[57] ABSTRACT

Apparatus for studying the interaction of first and second molecules in a test solution containing fluorescently labeled molecules in addition to the first and second molecules, with the first molecules and the fluorescently labeled molecules being capable of binding with the second molecules. The apparatus comprises a flow channel having opposite, spaced apart walls, with at least one of the walls or a portion thereof being translucent or transparent. A porous matrix is retained in a fixed position between the walls of the flow channel and in direct contact with a translucent or transparent portion of the walls of the flow channel. A test solution flows through the flow channel and around the porous matrix so as to be in contact with the porous matrix. The porous matrix comprises a material that is translucent or transparent and has pores or openings therein which are of a microscopic size such that the unbound fluorescently labeled molecules can permeate the porous matrix, while the second molecules and fluorescently labeled molecules bound to the second molecules cannot permeate the porous matrix. The porous matrix is substantially inert and does not react chemically with any of the molecules contained in the solution. Fluorescence emitted by the fluorescently labeled molecules permeating the porous matrix is detected through the translucent or transparent portion of the walls of the flow channel.

11 Claims, 2 Drawing Sheets

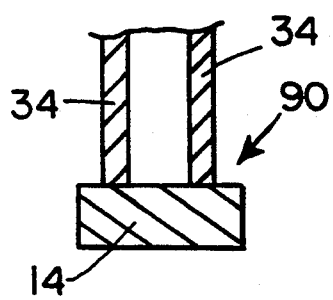
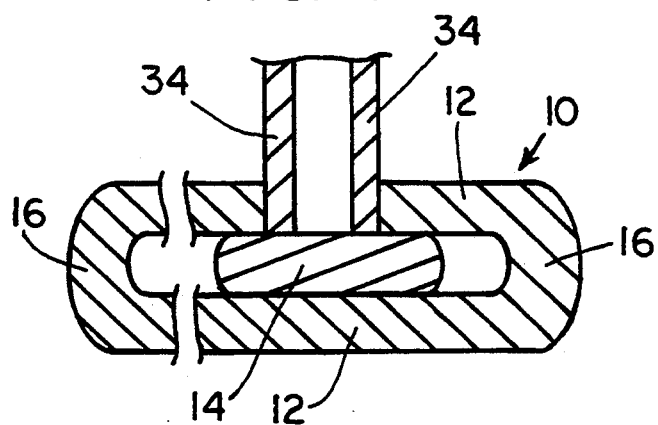
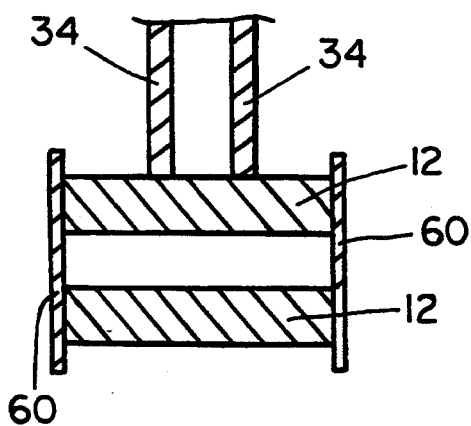
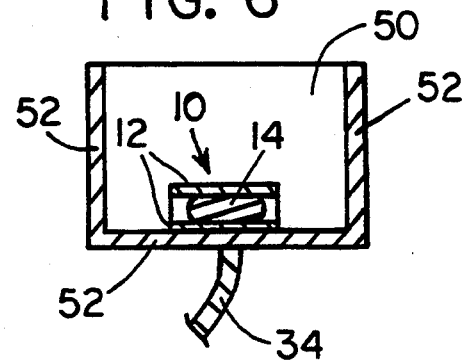
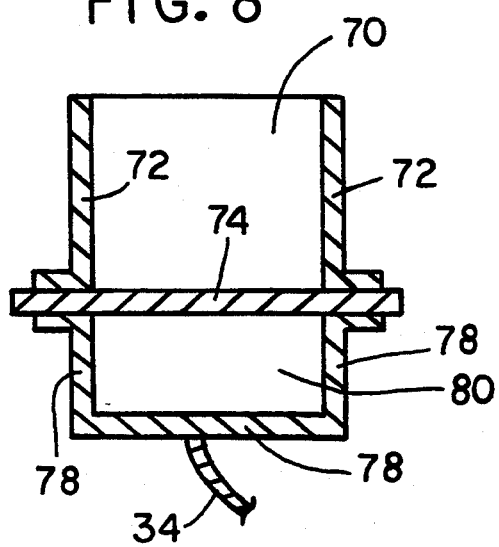
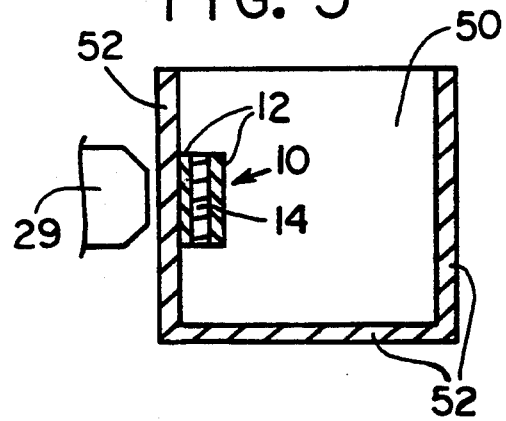

APPARATUS FOR USING FLUORESCENTLY LABELED LIGANDS IN STUDYING INTERACTION OF A NATIVE LIGAND AND ITS RECEPTOR

GOVERNMENT SUPPORT

This invention was made with Government support under Grant 5R01 GM38919-03 awarded by the National Institutes of Health. The Government has certain rights in the invention.

RELATED APPLICATION

This application is a continuation-in-part application of my copending application Ser. No. 07/668,237 filed Mar. 12, 1991, now U.S. Pat. No. 5,252,492. The entire contents of my copending application Ser. No. 07/668,237 are incorporated herein by reference.

BACKGROUND OF THE INVENTION

1. Field of the Invention

The present invention relates to a novel, simple and accurate apparatus for use in a method such as disclosed in my copending application Ser. No. 07/668,237 for studying interaction of a native ligand and its receptor. Such a method uses a fluorescently labeled, indicator ligand and a porous, optically transparent matrix that can be permeated by the fluorescently labeled ligand but is partially or totally impermeable to the labeled ligand when it is bound to the receptor. Fluorescence emitted from within the porous matrix is useful as an indicator of the interaction between the native ligand and the receptor.

2. State of the Art

Interaction of a ligand and a receptor in solution has been assayed or studied in the past by complicated techniques using differently labeled components. One such method is to use a radioactively labeled ligand or receptor. Another method is to utilize a fluorescent dye that is attached to the ligand or receptor. Generally, however, it has been necessary to isolate the reactants or products by complicated procedures. For example, special procedures have been necessary to separate bound from unbound ligands.

In U.S. Pat. No. 4,816,419 a method for fluorescence ligand binding assays is disclosed wherein certain surfactants that form micelles in solution were found to be useful in effecting differential fluorescence between bound and unbound ligands. The micelles sequester bound from unbound labeled ligands. Capture of labeled ligands occurs preferentially for free labeled ligands. When the labeled ligands are bound to a receptor, capture by the micelles is severely inhibited. The fluorescent emission is different when the labeled ligands are captured by the micelles than when the bound labeled ligands are not captured.

The method using the micelles of U.S. Pat. No. 4,816,419 is severely restricted in the breadth of ligands and receptors that can be analyzed or studied. The method employing the micelles is chemical in nature, thereby being restricted to the study of ligands and receptors bound to the ligands that interact in specific ways with the micelles. The ligands must be bound to or combine with the micelles, and the ligands bound to the receptor must not be attracted to or combine with the micelles.

In my copending application Ser. No. 07/668,237, a novel, simple, accurate, fast, economical method is disclosed for studying and assaying the interaction of two molecules, such as a ligand and its receptor, in solution utilizing the measurement of fluorescence within an optically transparent matrix that is differentially permeable to the molecules depending upon the size of the molecules. In the method of my copending application, a fluorescently labeled molecule is used that can permeate a porous, translucent or transparent matrix, with the reaction product of the labeled molecule and the other molecule being partially or totally excluded from the matrix. The matrix can then be viewed, such as through a fluorescence microscope, to determine fluorescence emitted from within the matrix.

3. Objective

The principal objective of the present invention is to provide novel apparatus for use in the method disclosed in my copending application Ser. No. 07/668,237.

BRIEF DESCRIPTION OF THE INVENTION

The present invention pertains to novel flow cell apparatus, test cells and test probes to be used in conducting the method of my copending application. That method as disclosed in application Ser. No. 07/668,237 involves the measurement of fluorescence within a porous matrix that is either translucent or transparent. The porous matrix is further differentially permeable to molecules depending on their sizes. Different matrixes may be used, such as dextran gels, polyacrylamide gels, cellulose membranes, porous glass or other porous, inert materials that can be substantially readily permeated by the one molecule but which hamper and inhibit permeation thereof by the other molecule. The fluorescence within the matrix is measured with various detector devices, including a conventional optical fluorescence microscope.

The matrix need only be sufficiently translucent so as to allow light to enter the matrix to excite fluorescently labeled molecules contained in the matrix and further allow the fluorescent light to be emitted from the matrix so that it can be detected and measured. Inasmuch as the overall thickness of the porous matrix is minimal, and because by appropriate focusing of the optics the fluorescently emitted light impinging on the detector can be restricted to emanate from only within several hundred microns of the surface of the matrix, even such relatively translucent materials such as cross-linked dextran can be used as the porous matrix.

The reagents in the study or assay are the receptor, the native ligand and a functional, fluorescently labeled, ligand (either the native ligand derivatized with a fluorescent reporter moiety, or a fluorescent analog of the native ligand). A matrix is selected which sterically excludes the receptor or the receptor-fluorescent ligand complex, but does not exclude the fluorescent ligand itself. When the matrix is immersed in a solution containing the fluorescent ligand alone, the fluorescent ligand will permeate the matrix and render the matrix fluorescent. However, when receptor is also in the solution, the fluorescence emitted by the matrix will be reduced because the fluorescent ligand bound to the receptor is totally or in part excluded from the matrix. On the other hand, if native ligand is also in the solution, it would preoccupy the receptor. Consequently, fewer fluorescent ligand molecules would be bound to receptor and therefor be excluded from the matrix. Thus, the presence of native ligand would be manifested by increased emission of fluorescence from the matrix.

In accordance with the present invention, novel flow cells, test cells and test probes are provided for rapidly and efficiently carrying out the fluorescent ligand exclusion analysis method of my copending application Ser. No. 07/668,237. In a preferred embodiment of the apparatus, a novel flow cell is provided that comprises opposite, spaced apart walls. At least one of the walls has a portion thereof which is translucent or transparent. A porous matrix is positioned between the walls of the flow channel so that the porous matrix is retained in a fixed position between the walls of the flow channel. The porous matrix is further positioned so that it is in contact with a translucent or transparent portion of the walls of the flow channel. Test solution flows through the channel so that the solution is in direct contact with the porous matrix and flows around the porous matrix. The fluorescence emitted by fluorescently labeled molecules that permeate the porous matrix can be detected through the translucent or transparent portion of the walls of the flow channel.

Although it is advantageous to make at least one of the walls (and generally both walls) of the flow channel of a translucent or transparent material, it is also contemplated that the walls of the flow channel could be made from an opaque material. If both walls of the flow channel are made of an opaque material, then a translucent or transparent window portion must be provided in at least one of the walls of the flow channel, with the window portion contacting the porous matrix. The more transparent the window, of course, more light can be transmitted to and from the porous matrix. However, translucent materials can be used provided they exhibit sufficient light transmittance to allow adequate light to pass through the wall or the window portion of the wall to the porous matrix to effect fluorescence of the fluorescently labeled molecules in the porous matrix, and further to allow fluorescence emitted by the porous matrix to be transmitted or passed back through the wall or the window portion of the wall so that the degree of fluorescence emitted by the porous matrix can be determined by an appropriate detector.

Additional objects and features of the invention will become apparent from the following detailed description, taken together with the accompanying drawings.

THE DRAWINGS

Preferred embodiments of the present invention representing the best modes presently contemplated of carrying out the invention are illustrated in the accompanying drawings in which:

FIG. 4 is a schematic, cross-sectional representation of a flow cell similar to that of FIG. 3 but showing the optical fiber extending through a wall of the flow cell into contact with the porous matrix element of the flow cell;

FIG. 5 is a schematic, cross-sectional representation of another preferred embodiment of a flow cell in accordance with the present invention in which the flow cell is associated with a test well for receiving samples of test solution;

FIG. 6 is a schematic, cross-sectional representation of a flow cell similar to that of FIG. 5 but which uses an optical fiber for transmitting the fluorescent light from the flow cell to a detecting device;

FIG. 7 is a schematic, cross-sectional representation of a test cell in accordance with the present invention wherein the cell comprising an enclosed space in which a portion of the walls of the cell are translucent or transparent and other portions of the walls are formed of semipermeable membranes;

FIG. 8 is a schematic, cross-sectional representation of a test probe in accordance with the present invention; and FIG. 9 is a schematic, cross-sectional representation of another embodiment of a test probe in accordance with the present invention.

DETAILED DESCRIPTION OF PREFERRED EMBODIMENTS

Figure 1:
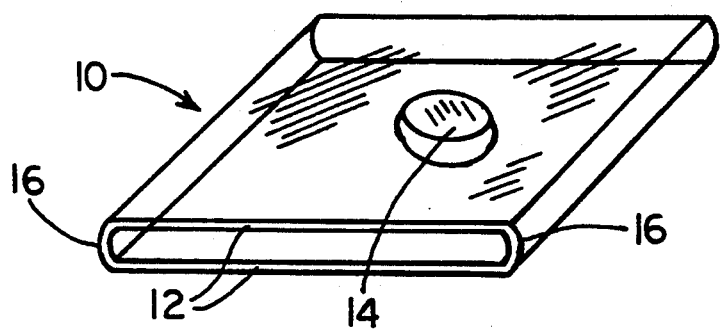
FIG. 1 is a pictorial representation of one preferred embodiment of a flow cell in accordance with the present invention.

The present invention provides novel test apparatus for use in studying the interaction of first and second molecules in a test solution, wherein the test solution contains fluorescently labeled molecules in addition to the first and second molecules, and the first molecules and the fluorescently labeled molecules are capable of binding with the second molecules. As illustrated in FIGS. 1–4, a flow cell in accordance with the present invention comprises a flow channel 10 formed by opposite, spaced apart walls 12. A porous matrix 14 is positioned between the walls 12 of the flow channel 10 so as to be retained in a fixed position between the walls 12 of the flow channel 10.

A test solution flows through the flow channel 10 so that the test solution is in contact with the porous matrix 14 and flows around the porous matrix. The porous matrix 14 consists of a material that has pores or openings therein which are of a microscopic size such that the fluorescently labeled molecules can permeate the porous matrix, while the second molecules and fluorescently labeled molecules bound to the second molecules cannot permeate the porous matrix 14. The porous matrix 14 is further substantially inert so that it does not react chemically with any of the molecules contained in the solution. Fluorescence emitted by unbound, fluorescently labeled molecules permeating the porous matrix 14 can be detected through the translucent or transparent portion of the walls 12 of the flow channel 10.

The flow channel 10 of FIGS. 1–4 advantageously is formed from a rectangular glass capillary, whereby the opposite walls 12 are formed of transparent glass, and the walls 12 have opposite, solid side edges 16 that hold the opposite walls 12 spaced apart from each other. It should be recognized that rectangular capillaries which are not made of transparent glass can also be used. For example, capillaries made of translucent material can be used.

If the walls 12 are made of a translucent material, that material must be capable of allowing light to pass through the wall 12 of the flow channel 10 to the porous matrix 14. The translucent material must further allow fluorescence emitted by the porous matrix 14 to pass back through the wall 12 of the flow channel 10 so that the fluorescence can be detected by an appropriate light detector such as a fluorescence microscope.

It is further noted that the flow channel 10 could be formed by opposite walls 12 that are made of an opaque material. If the walls 12 are opaque, then at least one window portion must be formed in at least one of the walls 12, with the window portion being made of a translucent or transparent material, and the porous matrix 14 must be positioned so that it is in direct contact with a window portion of the walls The rectangular glass capillary as illustrated in FIGS. 1-4 generally will have inner dimensions of about 40 by 400μ and a length of about 20 mm. However, these dimensions can vary widely depending on the particular application.

As illustrated in FIGS. 1-4, the opposite, open ends of the flow channel 10 formed by the rectangular capillary forms means for introducing a test solution into the flow channel 10. The test solution can flow through the capillary and around the porous matrix 14 that is positioned in the capillary.

Figure 2:
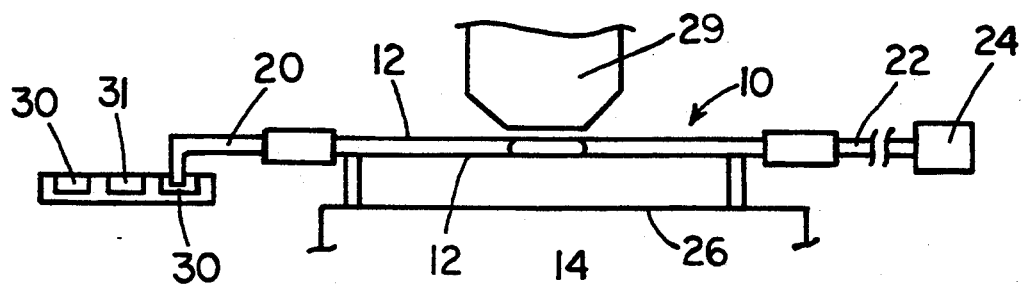
FIG. 2 is a schematic, elevational representation of the cell of FIG. 1 having further illustrating means for feeding test solutions and rinse solutions to the flow cell.

As shown in FIG. 2, it is advantageous to connect the open, upstream end of the capillary forming the flow channel 10 to the downstream end of a sample introduction conduit 20. A sample withdraw conduit 22 is attached at one end thereof to the open, downstream end of the capillary, and the downstream end of the withdraw conduit 22 is connected to a vacuum line or a suction pump 24.

The flow channel 10, as shown in FIG. 2, is conveniently mounted on a stage 26 of a fluorescence microscope which is preferably equipped with an epi-illuminator. The porous matrix 14 is positioned in optical alignment with the objective 29 of the fluorescence microscope so that the porous matrix can be continuously viewed or monitored while the flow channel 10 is being perfused. The intensity of the fluorescence emitted from within the porous matrix can be measured with a photodetector (not shown in the drawings), as is well known in the art.

The apparatus as illustrated in FIG. 2 can be advantageously used to rapidly test multiple samples of test solution. Each separate sample is placed in a separate sample well 30 (two such sample wells 30 are illustrated in FIG. 2, but a plurality of such wells can be provided). A rinse solution is placed in a separate rinse well 31 (one rinse well 31 is illustrated, but a plurality of such wells can be provided). The upstream end of the sample introduction conduit 20 can then be moved alternately between sample wells 30, however many of them as are desired, and the rinse well 31 so as to repeat the sequence of drawing a test solution into said flow channel 10 and then drawing rinse solution into the flow channel 10 in preparation for receiving a subsequent test solution. It should be recognized that the flow channel 10 could be mounted separate and apart from the stage of a microscope, and an optical fiber as will be discussed hereinafter can be linked between the flow channel 10 and the microscope to transmit illumination to the porous matrix as well as fluorescence from the porous matrix to the objective of the microscope.

The porous matrix 14 is preferably a gel that swells when hydrated, such as polyacrylamide. A bead of such material can be readily positioned within the flow channel 10 by filling the capillary forming the flow channel 10 with ethanol having at least one bead of the porous matrix suspended therein. The non-hydrated bead is of a size that it will readily enter into the flow channel 10. Water is allowed to diffuse into the flow channel 10 to replace the ethanol and hydrate the bead. The bead expands when hydrated, and the normal diameter of the bead when hydrated is much larger than the narrow dimension between the walls 12 of the flow channel 10. The hydrated bead that is caught between the walls 12 of the flow channel 10 assumes the shape of a right cylinder with barreled sides and is firmly wedged in place with its top and bottom flush against the walls 12 of the flow channel 10.

Figure 3:
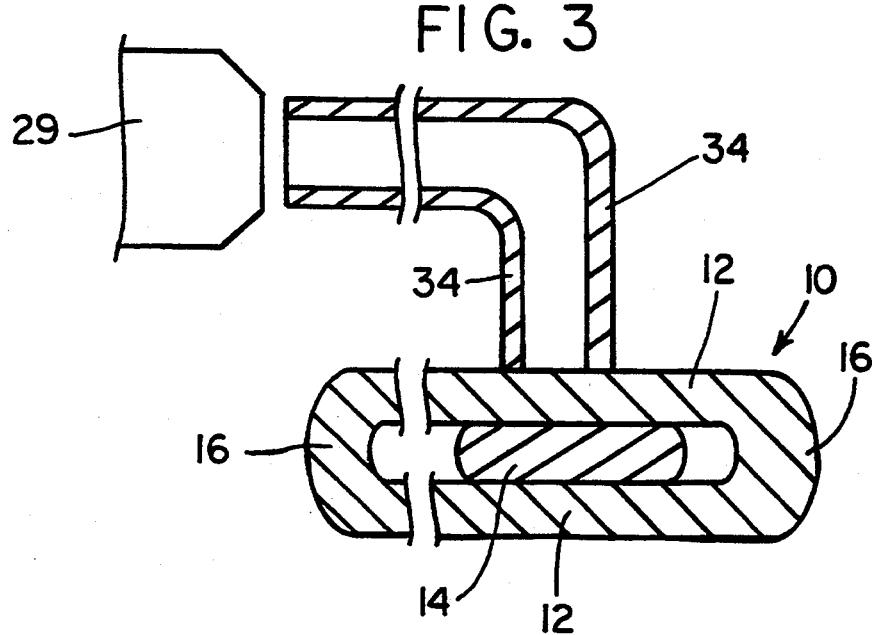
FIG. 3 is a schematic, cross-sectional representation of a flow cell similar to that of FIG. 1 wherein an optical fiber is associated with the flow cell.

As mentioned above, an optical fiber can be incorporated with the flow channel 10 so that the flow channel 10 does not have to be mounted adjacent to a light detector such as an objective of a fluorescence microscope. As illustrated in FIGS. 3 and 4, one end of the optical fiber 34 is glued to one of the walls 12 of the flow channel 10 so as to be in optical alignment with the porous matrix 14. The other end of the optical fiber 34 is associated with a combination light detector and illuminator, such as the objective 29 of a fluorescence microscope fitted with epi-illumination as is well known in the art.

If the walls 12 of the flow channel 10 are made from an opaque material, with a window portion of a translucent or transparent material being formed in the wall 12, then the porous matrix 14 and the one end of the optical fiber 34 must be in alignment with each other through the translucent or transparent window portion of the wall 12. A flow cell that can be adapted to have the walls 12 of the flow channel 10 being formed from either a translucent, transparent or an opaque material is shown in FIG. 4. An opening is formed in one wall 12 of the flow channel 10, and the porous matrix 14 is aligned with the opening in the wall 12 of the flow channel 10. The one end of the optical fiber 34 is received in the opening in the wall 12 of the flow channel 10 so that the one end of the optical fiber 34 is in alignment with and abuts against the porous matrix 14 in the flow channel 10.

The ends of the capillary of the flow channel 10 of the flow cell as illustrated in FIG. 1 can advantageously be trimmed so as to leave the flow channel 10 with a rather short dimension between opposed open ends of the capillary. Such a trimmed flow channel 10 can be placed in a test well 50 as shown in FIGS. 5 and 6. The test well 50 is formed of perimeter walls 52, and at least one of the perimeter walls 52 is formed of a translucent or transparent material, or a window portion is provided in one of the perimeter walls 52 that is formed of a translucent or transparent material. The term translucent has the same general meaning as given above when discussing the walls 12 of the flow channel 10.

The flow cell comprising the trimmed flow channel 10 is positioned in the test well 50 either on one of the side perimeter walls 52 as shown in FIG. 5 or on the bottom perimeter wall 52 as shown in FIG. 6. If the perimeter wall 52 of the test well 50 on which the flow channel 10 is positioned is not translucent or transparent, then the flow channel 10 is placed in alignment with a window portion of the perimeter wall 52 that is translucent or transparent. The translucent or transparent wall 12 of the flow channel 10 which is in contact with the porous matrix 14 is located adjacent to the perimeter wall 52 of the test well 50. If the perimeter wall 52 is opaque and has a translucent or transparent window portion, then the translucent or transparent wall 12 (or a translucent or transparent window portion thereof in those instances when the walls 12 of the flow channel 10 are made of an opaque material) is located adjacent to and in direct alignment with the translucent or transparent window portion of the perimeter wall 52 of the test well 50.

Test solution is introduced into the test wells 50 in the test apparatus illustrated in FIGS. 5 and 6, and because of the short distance between the open ends of the flow channel 10, the test solution readily enters the flow channel 10 by either capillary action or by diffusion. The fluorescence emitted by the fluorescently labeled, unbound molecules of the test solution that permeate the porous matrix 14 of the flow channel 10 can be detected through the aligned translucent or transparent portions of the flow channel 10 and the test well 50.

In the embodiment shown in FIG. 5, the flow cell 10 is located on an upstanding wall 52 of the test well 50. In FIG. 6, the flow channel 10 is shown positioned on the bottom wall 52 of the test well 50. An objective 29 of a microscope can be positioned in alignment with the flow channel 10 as shown in FIG. 5, or an optical fiber 34 can be attached to the test well 50 with one of the ends of the optical fiber being in optical alignment with the flow channel 10 as shown in FIG. 6. The other end of the optical fiber 34 is associated with a light detector, such as an objective of a microscope.

A test cell that can be positioned in a test well similar to the wells 50 of the test apparatus shown in FIGS. 5 and 6, but which is more advantageously adapted to be mobile so that it can be moved from one test well to another is shown in FIG. 7. The test cell of FIG. 7 comprises spaced apart, top and bottom walls 12 similar to the flow cells described previously. At least one of the top and bottom walls are translucent or transparent or have a window portion therein that is translucent or transparent.

A side boundary wall 60 encompasses the perimeters of the top and bottom walls 12 so as to enclose the space between the top and bottom walls. The boundary wall 60 is made, at least in part, from a semipermeable membrane that has pores or openings therein which are of a microscopic size such that when the semipermeable membrane contacts the test solution, the unbound fluorescently labeled molecules can permeate the semipermeable membrane and enter into the space between the top and bottom walls 12 of the test cell, while the second molecules and fluorescently labeled molecules that are bound to second molecules cannot permeate the semipermeable membrane and are prevented from entering into the space between the top and bottom walls 12 of the test cell.

The semipermeable membrane forming the boundary wall 60 is further made of a material that is substantially inert so that it does not react chemically with any of the molecules contained in the test solution. When the test cell illustrated in FIG. 7 is placed in the test solution, the amount of fluorescence emitted from fluorescently labeled molecules that enter the space between the top and bottom walls 12 of the test cell can be detected through the translucent or transparent portion of the top or bottom wall 12 of the test cell. The test cell of FIG. 7 preferably includes an optical fiber 34 having one end attached to a translucent or transparent portion of the top or bottom wall 12 of the test cell, with the other end of the optical fiber 34 being associated with a combination light detector and illuminator.

Another embodiment of a test cell that utilizes a semipermeable membrane is shown in FIG. 8. This test cell comprises a well 70 for receiving the test solution. The well 70 is formed by perimeter sidewalls 72 and a bottom wall 74. The bottom wall 74 is made from a semipermeable membrane. The semipermeable membrane forming the bottom wall 74 has the same characteristics as those of the semipermeable membrane that forms the boundary wall 60 of the embodiment shown in FIG. 7.

A sub-chamber 80 is formed below the semipermeable membrane forming the bottom wall 74 of well 70, with the sub-chamber 80 being formed by perimeter walls 78. At least a part of at least one of the perimeter walls 78 of the sub-chamber 80 is translucent or transparent. That is, one of the walls 78 is translucent or transparent of a window portion is provided in one of the walls 78 that is made from a translucent or transparent material.

When a test solution is placed in well 70 of the test cell of FIG. 8, unbound, fluorescently labeled molecules in the test solution permeate the semipermeable membrane forming the bottom wall 74 of well 70 and enter the sub-chamber 80. The amount of fluorescence emitted by the fluorescently labeled molecules in the sub-chamber 80 can be detected through the translucent or transparent portion of the perimeter wall 78 of the sub-chamber 80. The test cell preferably includes an optical fiber 34 having one end attached to the translucent or transparent portion of the perimeter wall 78 of the sub-chamber 80, with the other end of the optical fiber 34 being associated with a combination light detector and illuminator.

A simple test probe 90 in accordance with the present invention that can be rapidly moved from one test solution to another is shown in FIG. 9. The test probe 90 comprises an optical fiber 34 that has one end thereof associated with a combination light detector and illuminator such as the objective of a fluorescence microscope fitted for epi-illumination. A relatively small piece of porous matrix 14 is attached directly to the other end of the optical fiber 34. The porous matrix 14 has the same characteristics as stated hereinbefore for the porous matrix counterpart of the embodiments of the invention shown in FIGS. 1-4. When the end of the optical fiber 34 having the porous matrix 14 is immersed in a test solution, the amount of fluorescence emitted by unbound, fluorescently labeled molecules that permeate the porous matrix 14 can be detected through the optical fiber 34.

Although preferred embodiments of the method of the present invention have been illustrated and described, it is to be understood that the present disclosure is made by way of example and that various other embodiments are possible without departing from the subject matter coming within the scope of the following claims, which subject matter is regarded as the invention.

What is claimed is:

1. A flow cell for use in studying the interaction of first and second molecules in a test solution, wherein the test solution contains fluorescently labeled molecules in addition to the first and second molecules, and the first molecules and the fluorescently labeled molecules are capable of binding with the second molecules, said flow cell comprising a flow channel consisting of a rectangular capillary having opposite, spaced apart walls, with at least one of said walls having at least a portion thereof which is translucent or transparent;

means for detecting fluorescence, said means for detecting fluorescence being in direct or functional contact with said translucent or transparent portion;

a porous matrix in the form of a bead that is translucent or transparent and is positioned between the walls of the flow channel so that the bead is wedged in a fixed position between the opposite walls of the flow channel, said porous matrix bead further being in direct contact with a translucent or transparent portion of said walls of said flow channel;

means for introducing a test solution into said flow channel so that the test solution is in contact with said porous matrix and flows around said porous matrix;

said porous matrix bead consists of a material that has pores or openings therein which are of a microscopic sir such that the unbound fluorescently labeled molecules can permeate said porous matrix bead, while the second molecules and fluorescently labeled molecules bound to the second molecules cannot permeate said porous matrix bead, with said porous matrix bead further being substantially inert so that it does not react chemically with any of the molecules contained in said solution;

whereby the fluorescence emitted by the fluorescently labeled molecules permeating said porous matrix can be detected through said translucent or transparent portion of the walls of said flow channel.

2. A flow cell in accordance with claim 1 further including
a sample introduction conduit having first and second ends, with the second end thereof being in flow communication with an upstream open end of said flow channel; and
a sample withdraw conduit having first and second ends, with the first end thereof being in flow communication with a downstream open end of said flow channel.

3. A flow cell in accordance with claim 2 further including a suction pump in flow communication with the second end of said sample withdraw conduit.

4. A flow cell in accordance with claim 3 further including a plurality of sample wells that can contain samples of test solutions and rinse solutions, whereby the first end of said sample introduction conduit can be moved alternately between sample wells containing a test solution and a rinse solution so as to repeat the sequence of drawing a test solution into said flow cell and then drawing rinse solution into said flow cell in preparation for receiving a subsequent test solution.

5. A flow cell for use in studying the interaction of first and second molecules in a test solution, wherein the test solution contains fluorescently labeled molecules in addition to the first and second molecules, and the first molecules and the fluorescently labeled molecules are capable of binding with the second molecules, said flow cell comprising
a flow channel having opposite, spaced apart walls, with at least one of said walls having at least a portion thereof which is translucent or transparent;
said flow cell also having opposite sides joining opposite side edges of said walls to hold the opposite walls spaced apart from each other;
a porous matrix that is translucent or transparent and is positioned between the walls of the flow channel so as to be retained in a fixed position between said walls of the flow channel, said porous matrix further being in direct contact with a translucent or transparent portion of said walls of said flow channel;

means for introducing a test solution into said flow channel so that the test solution is in contact with said porous matrix and flows around said porous matrix, said means for introducing the test solution into said flow channel comprising open ends of the flow channel through which the test solution can flow into and out of the flow cell;

an optical fiber having one end attached to a translucent or transparent portion of said walls that is in contact with said porous matrix, with said one end of said fiber optical fiber being in optical alignment with the porous matrix, and with the other end of said optical fiber being associated with a light detector said porous matrix consists of a material that has pores or openings therein which are of a microscopic size such that the unbound fluorescently labeled molecules can permeate said porous matrix, while the second molecules and fluorescently labeled molecules bound to the second molecules cannot permeate said porous matrix, with said porous matrix further being substantially inert so that it does not react chemically with any of the molecules contained in said solution, whereby the fluorescence emitted by the fluorescently labeled molecules permeating said porous matrix can be detected through said translucent or transparent portion of the walls of said flow channel.

6. A flow cell in accordance with claim 5 wherein an opening is provided in the translucent or transparent portion of the wall to which said one end of the optical fiber is attached, with the one end of the optical fiber being received in the opening so that said one end of the optical fiber is positioned adjacent to said porous matrix.

7. A flow cell in accordance with claim 5 further including
a sample introduction conduit having first and second ends, with the second end thereof being in flow communication with an upstream open end of said flow channel; and
a sample withdraw conduit having first and second ends, with the first end thereof being in flow communication with a downstream open end of said flow channel.

8. A flow cell in accordance with claim 7 further including a suction pump in flow communication with the second end of said sample withdraw conduit.

9. A flow cell in accordance with claim 8 further including a plurality of sample wells that can contain samples of test solutions and rinse solutions, whereby the first end of said sample introduction conduit can be moved alternately between sample wells containing a test solution and a rinse solution so as to repeat the sequence of drawing a test solution into said flow cell and then drawing rinse solution into said flow cell in preparation for receiving a subsequent test solution.

10. A flow cell for use in studying the interaction of first and second molecules in a test solution, wherein the test solution contains fluorescently labeled molecules in addition to the first and second molecules, and the first molecules and the fluorescently labeled molecules are capable of binding with the second molecules, said flow cell comprising
a flow channel having opposite, spaced apart walls, with at least one of said walls having at least a portion thereof which is translucent or transparent;

said flow cell also having opposite sides joining opposite side edges of said walls to hold the opposite walls spaced apart from each other;

a porous matrix that is translucent or transparent positioned between the walls of the flow channel so as to be retained in a fixed position between said walls of the flow channel, said porous matrix further being in direct contact with a translucent or transparent portion of said walls of said flow channel;

means for introducing a test solution into said flow channel so that the test solution is in contact with aid porous matrix and flows around said porous matrix, said means for introducing the test solution into said flow channel comprising open ends of the flow channel through which the test solution can flow into and out of the flow cell;

a well formed from perimeter walls, with at least one of said perimeter wall having at least a portion thereof which is translucent or transparent, and the flow cell is positioned within said well, with the translucent or transparent portion of the wall of the flow cell which is in contact with said porous matrix being located adjacent to and in direct alignment with the translucent or transparent portion of the perimeter wall of said well, whereby the test solution can be introduced into said well so as to diffuse into said flow cell through the open ends of said flow cell and the fluorescence emitted by the fluorescently labeled molecules permeating said porous matrix can be detected through the aligned translucent or transparent per%ions of said flow cell and said well;

mean or detecting fluorescences, said means for detecting fluorescence being in direct or functional contact with said translucent or transparent portion of said well, said porous matrix consist of a material that has pores or openings therein which are of a microscopic size such that the unbound fluorescently labeled molecules can permeate said porous matrix, while the second molecules and fluorescently labeled molecules bound to the second molecule cannot permeate said porous matrix, with said porous matrix further being substantially inert so that it does not react chemically with any of the molecules contained in said solution, whereby the fluorescence emitted by the fluorescently labeled molecules permeating said porous matrix can be detected through said translucent or transparent portion of the walls of said flow channel.

11. A flow cell in accordance with claim 10 further including an optical fiber having one end attached to the translucent or transparent portion of the wall of said well which is in alignment with the translucent or transparent portion of the wall of the flow cell that is in contact with said porous matrix, with said one end of said optical fiber being in optical alignment with the porous matrix of said flow cell, and with the other end of said optical fiber being associated with a light detector.

* * * * *